United States Patent
O'Neill et al.

(10) Patent No.: US 12,133,802 B2
(45) Date of Patent: Nov. 5, 2024

(54) ORTHOPAEDIC TRAUMA PLATE AND METHOD FOR FORMING SAME

(71) Applicants: National University of Singapore, Singapore (SG); National University Hospital (Singapore) Pte Ltd, Singapore (SG)

(72) Inventors: Gavin Kane O'Neill, Singapore (SG); Lina Yan, Singapore (SG)

(73) Assignees: National University of Singapore, Singapore (SG); National University Hospital (Singapore) Pte Ltd, Singapore (SG)

( * ) Notice: Subject to any disclaimer, the term of this patent is extended or adjusted under 35 U.S.C. 154(b) by 467 days.

(21) Appl. No.: 17/438,562

(22) PCT Filed: Mar. 13, 2020

(86) PCT No.: PCT/SG2020/050134
§ 371 (c)(1),
(2) Date: Sep. 13, 2021

(87) PCT Pub. No.: WO2020/185168
PCT Pub. Date: Sep. 17, 2020

(65) Prior Publication Data
US 2022/0362027 A1 Nov. 17, 2022

(30) Foreign Application Priority Data
Mar. 13, 2019 (SG) .......................... 10201902254Y

(51) Int. Cl.
*A61F 2/30* (2006.01)
*B22F 10/28* (2021.01)
(Continued)

(52) U.S. Cl.
CPC ........ *A61F 2/3094* (2013.01); *A61F 2/30942* (2013.01); *B22F 10/80* (2021.01);
(Continued)

(58) Field of Classification Search
CPC ................ A61F 2/3094; A61F 2/30942; A61F 2002/30014; A61F 2002/30322;
(Continued)

(56) References Cited

U.S. PATENT DOCUMENTS 10,675,158 B2    6/2020  Unger et al.
2007/0238069 A1  10/2007 Lovald et al.
(Continued)

FOREIGN PATENT DOCUMENTS

CN       1424893 A    6/2003
CN     106456331 A    2/2017
(Continued)

OTHER PUBLICATIONS

S. P. Singh, T. Bhardwaj and M. Shukla, "Lattice modeling and finite element simulation for additive manufacturing of porous scaffolds," 2017 International Conference on Advances in Mechanical, Industrial, Automation and Management Systems (AMIAMS), Allahabad, India, 2017, pp. 333-336 (Year: 2017).*
(Continued)

*Primary Examiner* — Mohammad Ali
*Assistant Examiner* — Dhruvkumar Patel
(74) *Attorney, Agent, or Firm* — Botos Churchill IP Law LLP

(57) ABSTRACT

Disclosed is a method for forming an orthopaedic implant. The method comprises determining one or more parameters of a bone, of a subject, to which the implant is to be attached, and calculating specifications based on parameters. That calculation includes calculating a mechanical property relating to elasticity of the implant, a length of the implant, and
(Continued)

positions of two or more fixation locations by which to fix the implant to the bone. The method further comprises forming the implant based on the specifications, wherein each fixation location comprises a longitudinal axis through the implant, and calculating specifications comprises calculating a trajectory for the longitudinal axis of the respective fixation location.

9 Claims, 13 Drawing Sheets

(51) Int. Cl.
| | |
|---|---|
| *B22F 10/36* | (2021.01) |
| *B22F 10/366* | (2021.01) |
| *B22F 10/66* | (2021.01) |
| *B22F 10/80* | (2021.01) |
| *B33Y 80/00* | (2015.01) |

(52) U.S. Cl.
CPC ..... *B33Y 80/00* (2014.12); *A61F 2002/30014* (2013.01); *A61F 2002/30322* (2013.01); *A61F 2002/30784* (2013.01); *A61F 2002/3093* (2013.01); *A61F 2002/30943* (2013.01); *A61F 2002/30955* (2013.01); *A61F 2002/30985* (2013.01); *B22F 10/28* (2021.01); *B22F 10/36* (2021.01); *B22F 10/366* (2021.01); *B22F 10/66* (2021.01)

(58) Field of Classification Search
CPC .... A61F 2002/30784; A61F 2002/3093; A61F 2002/30943; A61F 2002/30955; A61F 2002/30985; A61F 2002/30004; A61F 2002/30006; A61F 2002/30011; A61F 2002/30777; A61F 2002/30838; A61F 2002/3092; A61F 2/30767; A61F 2002/3432; Y02P 10/25; A61B 17/80; B22F 3/1115; B33Y 10/00

See application file for complete search history.

(56) References Cited

U.S. PATENT DOCUMENTS

| | | | |
|---|---|---|---|
| 2007/0276501 A1* | 11/2007 | Betz | A61F 2/30942 264/222 |
| 2014/0081400 A1* | 3/2014 | Azernikov | G06T 19/20 703/1 |
| 2015/0051650 A1* | 2/2015 | Verstreken | G16Z 99/00 606/281 |
| 2015/0272598 A1 | 10/2015 | Dubois et al. | |
| 2016/0256279 A1* | 9/2016 | Sanders | A61F 2/28 |
| 2017/0020685 A1* | 1/2017 | Geisler | A61F 2/30965 |
| 2017/0143494 A1* | 5/2017 | Mahfouz | A61F 2/34 |
| 2018/0206895 A1* | 7/2018 | Windolf | A61B 17/8061 |
| 2019/0209327 A1* | 7/2019 | Fitzpatrick | A61L 27/06 |
| 2019/0269445 A1* | 9/2019 | Singh | A61B 17/8057 |
| 2020/0146616 A1* | 5/2020 | Bowman | G06F 9/455 |
| 2020/0163703 A1* | 5/2020 | Sperling | A61B 17/8061 |
| 2020/0237418 A1* | 7/2020 | Courtney, Jr. | A61B 17/808 |

FOREIGN PATENT DOCUMENTS

| | | | |
|---|---|---|---|
| CN | 109199644 A | | 1/2019 |
| KR | 20190100837 A | * | 8/2019 |
| WO | 2015131234 A1 | | 9/2015 |
| WO | 2017077315 A2 | | 5/2017 |

OTHER PUBLICATIONS

The International Search Report and The Written Opinion of the International Searching Authority for PCT/SG2020/050134, Date of Mailing: Jun. 12, 2020.

Rodgers, et al., "Optimizing Porous Lattice Structures for Orthopaedic Implants", Conf Proc IEEE Eng Med Biol Soc., 2015, pp. 2450-2453.

Singh, et al., "Lattice Modeling and Finite Element Simulation for Additive Manufacturing of Porous Scaffolds", IEEE Conference on Advances in Mechanical, Industrial, Automation and Management Systems, 2017, pp. 382-385.

* cited by examiner

S. Min. Principal (Avg. 75%)
+6.480x10$^1$ (node 3487)
...
-5.661x10$^2$ (node 3398)
Max: +6.480x10$^1$
  Elem: Assem3 with gap
  and default-1.89596
Min: -5.661x10$^2$
  Elem: Assem3 with gap
  and default-1.89593

(a)

S. Min. Principal (Avg. 75%)
+1.790x10$^1$ (node 383)
...
-3.963x10$^2$ (node 29090)
Max: +1.790x10$^1$
 Elem: Plate-1.59774
Min: -3.963x10$^2$
 Elem: Plate-1.5487

(b)

|  | Truss-1 126 | Truss-2 128 | Truss-3 130 |
|---|---|---|---|
| Lattice unit | | | |
| Top view x-y | | | |
| Side view y-z | | | |

(a)

|  | Bio-1 132 | Bio-2 134 | Bio-3 136 | Bio-4 138 | Bio-5 140 |
|---|---|---|---|---|---|
| Lattice unit | | | | | |
| Top view x-y | | | | | |
| Side view y-z | | | | | |

Front View  Back View (c)

(a)

(b)

×××represent XCT plane fitting (a)

(b)

(c)

(c)

(d)

(a)

(b)

(c)

ORTHOPAEDIC TRAUMA PLATE AND METHOD FOR FORMING SAME

CROSS-REFERENCE TO RELATED APPLICATIONS

The present application is a national phase entry under 35 U.S.C. § 371 of International Application No. PCT/SG2020/050134, Mar. 13, 2020, published as International Publication No. WO 2020/185168 A1, which claims the benefit of the filing date of Singapore Patent Application No. 10201902254Y filed Mar. 13, 2019, the disclosures of which are hereby incorporated by reference.

TECHNICAL FIELD

The present invention relates to orthopaedic trauma plates and methods for forming orthopaedic trauma plates.

BACKGROUND

Fracture fixation and the devices we use for this have not changed substantially over the past 20-30 years. Fractures can be 'fixed' in a number of ways. One of the most common techniques used is open reduction and internal fixation using either medical grade stainless steel 316L or Ti-6Al-4V plates.

These plates are currently manufactured using standard casting/forging and post processing techniques. The plates produced have a number of issues. They are much stiffer than bone, the discrepancy in modulus of elasticity between the implant and bone can cause delayed union or even non-union. They are manufactured in predetermined sizes with a fixed number of holes. No variability in size/shape or hole location is possible. If fractures do not heal in a timely fashion then the redundant or unused holes in the plate can become a stress raiser, potentially leading to failure of the implant.

Bone plates were used in fracture fixation from the 19$^{th}$ century, and their shapes and locking mechanisms were innovated over years. A large number of bone plate designs were patented by medical companies. For example, U.S. Pat. Nos. 5,709,686A, 6,454,770B1, and US20060235400A1 were granted to Synthes USA LLC in 1995, 2002, and 2006. For all those bone plate designs, only standard sizes and lengths are available on market. Redundant screw holes are prepared to satisfy diverse types of fractures, which further act as stress raisers due to stress concentration around empty screw holes as shown in our finite element analysis (FEA) study (FIG. 1, FIG. 2 and FIG. 3).

Furthermore, clinical applications of traditional bone plates suffer from stress-shielding problems due to the high mismatching of modulus between fixation plates and human bone. The young's modulus of stainless steel is about 190 GPa, while the value for cortical bone only barely reaches about 20 GPa. In addition, in some special cases such as peri-articular fractures, bending irons and pliers are used to contour the plate to the anatomy.

SUMMARY OF THE INVENTION

Disclosed herein is a method for forming an orthopaedic implant, comprising:
determining one or more parameters of a bone, of a subject, to which the implant is to be attached;
calculating specifications based on parameters comprising:
a mechanical property relating to elasticity of the implant;
a length of the implant; and
positions of two or more fixation locations by which to fix the implant to the bone; and
forming the implant based on the specifications
wherein each fixation location comprises a longitudinal axis through the implant, and calculating specifications comprises calculating a trajectory for the longitudinal axis of the respective fixation location.

The mechanical property may be calculated further based on an expected natural flexibility of the bone.

The method may further comprise determining the weight of the subject and determining the expected natural/optimal flexibility/strain of the bone/fracture based on this.

Each fixation location may comprise a longitudinal axis through the implant, and calculating specifications comprising positions of the two or more fixation locations comprises calculating a trajectory for the longitudinal axis of the respective fixation location.

Each fixation location may be arranged to co-operate with a screw, either locking or non-locking, to anchor the implant to the bone, and the trajectory is calculated to guide the screw into the bone along an optimal anchoring direction.

Calculating specifications comprising positions of the two or more fixation locations may comprise determining relative positions of the fixation locations to reduce creation of localised stresses in the bone after fixation of the implant thereto.

Forming the implant may comprise using 3-dimensional printing to build the implant.

Forming the implant based on the mechanical property relating to elasticity of the implant may comprise forming the implant with an internal lattice structure to maintain outer dimensions and overall strength of the implant while reducing resistance to bending.

Forming the implant may comprise forming a solid shell with the internal lattice structure in the solid shell. The solid shell may fully enclose the internal lattice structure. The solid shell may alternatively be open, comprising a solid edge and back of the implant, and a front of the implant is at least partially omitted so the lattice structure is at least partially exposed to the bone.

Forming the implant may comprise selecting a type of lattice structure to promote osteoinduction. Forming the implant may comprise selecting a type of lattice structure to promote osteoconduction.

The bone may comprise a fracture and the implant may thus be a plate secured across the fracture.

Forming the plate may comprise modifying topography of a surface of the plate to promote osteoinduction. Forming the plate may comprise modifying topography of a surface of the plate to promote osteoconduction. It may be the surface of the plate facing the fracture site that is, in use, modified.

Calculating specifications may include using finite element analysis to determine properties of the implant to cooperate with the one or more parameters.

Also described herein is a system comprising memory and at least one processor, the memory storing instructions that, when executed by the at least one processor, cause the system to perform the method described above.

There may also be provided an orthopaedic implant may be formed using the method described above.

There may also be provided an orthopaedic trauma plate may be formed using the method described above.

Also described herein is an orthopaedic implant formed for a specific subject, the implant being formed in accordance with specifications, the specifications comprising an elasticity, a length and positions of two or more fixation locations by which to fix the implant to a bone of the subject, the specifications being determined from the bone of the subject, wherein each fixation location comprises a longitudinal axis through the implant along a trajectory calculated determined to optimise an anchoring direction of an anchor used with the implant.

The elasticity may be calculated based on an expected natural flexibility of the bone. The elasticity may be calculated based on a weight of the subject.

Each fixation location may be arranged to cooperate with a respective screw.

The fixation locations may be located relative to one another to reduce creation of localised stresses in the bone after fixation of the implant thereto.

The implant may further comprise an internal lattice structure to maintain outer dimensions of the implant while reducing resistance to bending.

The implant may further comprise a solid shell with the internal lattice structure in the solid shell. The solid shell may fully enclose the internal lattice structure. The solid shell may be open and formed as a solid edge and back of the implant, and a front of the implant is at least partially omitted so the lattice structure is at least partially exposed to the bone. A type of the lattice structure may be selected to promote one or both of osteoinduction and osteoconduction.

A surface topography of the implant may be modified to promote one or both of osteoinduction and osteoconduction.

The implant may be an orthopaedic trauma plate.

BRIEF DESCRIPTION OF THE DRAWINGS

Some embodiments will now be described by way of non-limiting example only, with reference to the accompanying drawings in which:

FIG. 5 illustrates optimised internal lattices, (a) truss-based internal lattices, and (b) bio-inspired lattices;

DETAILED DESCRIPTION

Using implants and plates described herein, problems with conventional plates can be overcome using additive manufacturing (AM) or 3-dimensional printing. Disclosed herein are orthopaedic plates designs of which allow the user/manufacturer to manipulate the Young's modulus of a plate by using self-supporting internal lattice structures instead of solid metal. This can be done while maintaining sufficient bending strength of the plate. In addition to this the AM process allows the user to alter the design of the plate, potentially removing unnecessary holes and placing the effective holes at optimised fixation locations.

The mechanical property advantages of plates and implants disclosed herein may translate into improved rates of fracture union and a shorter time to union, either when used in a mass production process via AM or in a customised setting.

The following description will be made generally with reference to a "plate", though it will be understood the present teachings can be applied to other orthopaedic implants.

Figure 17:
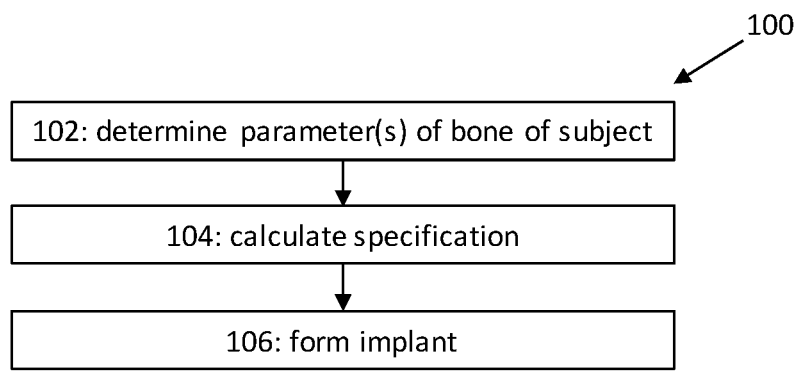
FIG. 17 illustrates the broad steps of a method for forming an implant in accordance with present teachings.

The present invention provides an effective methodology to facilitate fast customization of orthopaedic implant from design to manufacturing. In a broad sense, the method 100 for forming an orthopaedic implant comprises the steps set out in FIG. 17, namely:

Step 102: determining parameter(s) of a bone of the subject to which the implant is to be attached;

Step 104: calculating various specifications to facilitate formation of the implant; and Step 106: forming the implant based on the specifications calculated at step 104.

Step 102 may involve calculating an expected natural flexibility of the bone of the subject. The expected natural flexibility is the flexibility—e.g. Young's modulus—of the bone sought to be repaired. This calculation may involve measuring the weight of the subject or the bone size, or inferring the bone size—e.g. from the height and/or weight of the patient, patient age, and other factors. Step 104 then includes calculating a mechanical property relating to the elasticity of the implant—e.g. Young's modulus—based on the expected natural flexibility.

By tailoring the flexibility of the implant to compliment that of bone of the subject—e.g. have the same flexibility or modulus—the implant is less susceptible to breakage. For example, it will not be so weak that it will break during use of the bone. In addition, the implant will flex in a manner similar to that of the bone being repaired which promotes healing of the bone. It will therefore not be so rigid as to create substantial stress raisers in the bone that may inhibit healing or create new fracture sites.

Step 102 may also include determining the length of the bone or of the fracture, the diameter or shape of the bone to permit the shape of the implant to be tailored to fit, porosity (e.g. for patients with osteoporosis), and other parameters.

Once parameters of the bone have been determined, specification can then be calculated (Step 104) based on the parameters. In general, the specifications will include a mechanical property of the implant, relating to its elasticity—e.g. to ensure flexibility is matched to that of the bone being repaired—a length of the implant and the positions of fixation locations by which the implant is to be fixed to the bone.

In practice, after performing Step 102, the method will usually involve five parts. Step 104 can be performed by (Part (1)) the computer-aided design (CAD) of a plate or other orthopaedic implant. The size (e.g. length) and shape of the plate can be refined with reference to patient height, weight, fracture modelling constructed from CT scanning data (per Step 102), as well as FEA analysis of stress distribution on a standard plate. Also per Step 104, (Part (2)) the fixation number and locations can then be determined. In general, the fixation locations will be screw holes though, for small bones, the fixation locations may be better suited to the application of adhesive or ties. In the case of screw holes and similar, each fixation location will comprise a longitudinal axis through the implant—this will coincide with the axis of the screw or fastener cooperating with the hole as the implant is fixed to the bone. Part (2) of Step 104 therefore involves calculating trajectories of the longitudinal axes of the fixation locations through the implant—i.e. in the direction of the bone such that the implant can be held against the bone and a fastener driven into the bone, through the implant.

In this manner, the fixation locations can cooperate with fasteners—e.g. screws—to anchor the implant to the bone, and to guide the fasteners into the bone along an optimal anchoring direction as determined by the trajectories calculated at Step 104. Notably, where a standard plate has fixed, generally parallel screw holes extending perpendicularly through the plate, such trajectories are rarely optimal for anchoring the plate to bone of varying size and fracture shape. By customising—e.g. determining relative locations of the fixation locations to reduce or minimise localised stresses in the bone after fixation of the implant thereto—the number of screw holes can potentially be reduced, smaller diameter screws may be used and/or the implant will better cooperate with the bone to promote healing.

The location and number of screw holes on the plate can be customized by reference to the parameters defined at Step 102 and/or specifications (mechanical property(ies), length etc) calculated at step 104, to optimise the fixation as well as to minimise stress concentration. The plate can also be contoured to fit or cooperate with anatomy on a stereolithography (STL) file, or other type of file, to further improve the fitting of the implant to the bone.

Step 106 involves designing the implant using the specifications determined at Step 104. In this regard, designs in accordance with present teachings can make use of 3-dimensional (3D) printing to build the implant per Step (4), discussed below. In particular, the implant may be formed, based on the mechanical property determined at Step 104 (e.g. elasticity or modulus of the implant) to have an internal lattice structure. The internal lattice structure enables the outer dimensions of the implant to be maintained (e.g. in accordance with standard dimensions of orthopaedic trauma plates) while reducing resistance to bending.

In some cases, the implant may be designed per Step 106 to have a solid shell with the internal lattice structure in the solid shell—e.g. the lattice structure is completely hidden or fully enclosed by a solid shell the design of which may include designing the fixation locations so that the internal lattice structure is not exposed therein and to maintain the ability of the fixation locations to grasp the fasteners for anchoring the implant to the bone, as indicated by plates 108 in FIG. 6c.

In other cases, the implant may be designed per Step 106 to have a solid shell that is open (i.e. not fully enclosing the lattice). In these cases, the solid shell may have a solid edge as indicated by reference numeral 110 in FIG. 6c, with a solid back 112 (i.e. the face of the implant facing away from the bone when attached thereto) and a front that is at least partially omitted so the lattice structure 114 is at least partially exposed to the bone. The structure of the lattice can therefore be selected to promote osteoinduction and/or osteoconduction whereas, in the fully enclosing solid shell example, the surface facing the fracture may be textured or otherwise formed to promote osteoinduction and/or osteoconduction.

Thus, Step 106 involves (Part (3)) selecting the optimal internal lattices to customize the modulus and bending structural stiffness of the plate—mathematical predictions of the modulus of the bone and/or of the plate can be used as a guideline, rather than forming and testing individual implants. Step 106 further involves (Part (4)) printing the bone plate using AM techniques. Once printed, the plate can be cleaned per the requirements of relevant standards—e.g. (Part (5)) FDA and ASTM standards.

Figure 1:
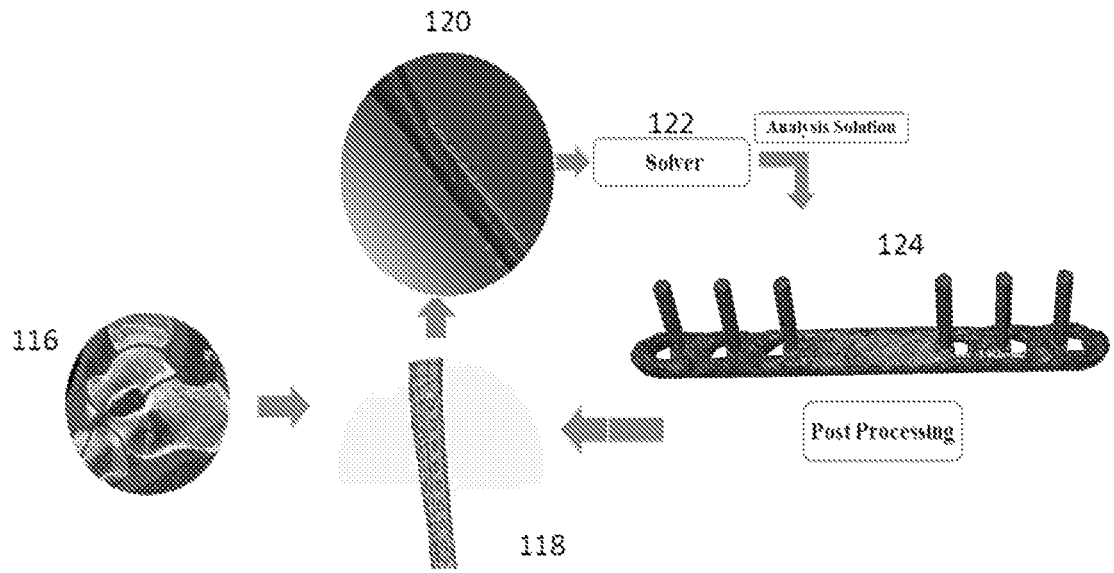
FIG. 1 illustrates a methodology for FEA.

In Part (1) of Step 104, CAD design of the plate can be achieved using commercially available design software. In this sense, some embodiments of the invention involve the adaptation of a standard bone plate—e.g. using a standard bone plate as a template and then applying customizations to it in a manner in accordance with present teachings. The plate design can be further refined with reference to patient specific weight, 3D fracture modelling, and FEA studies. One example of FEA analysis is illustrated in FIG. 1. The bone geometry model was constructed from CT (computer tomography) scanning of human tibia cadaver using medical image processing software—116. A standard plate was fitted to the bone geometry—118—and finite element modelling was conducted—120. This involves geometry editing, defining material properties, applying forces (loading and boundary conditions) and create FE model (meshing). The result of step 120 was passed through a solver—122—and the solution analysed to determine properties of the installed plate and the plate was then modelled subject to loading—124. The model is post-processed after loading and steps are repeated until a stable solution (e.g. further modifications are within a threshold that is sufficiently low to assume negligible variance in the solution from further repetitions of the steps) is produced. The stress distribution on standard narrow plate and broad bone plate with two empty screw holes is demonstrated in FIGS. 2(a) and 3(a) respectively, with screw holes in place, and in FIGS. 2(b) and 3(b) respectively, without screw holes. Furthermore, it is clearly indicated that, by removing two redundant screw holes, stress concentration can be relieved, and therefore the risk of failure can be reduced (FIG. 2b and FIG. 3b). In FIG. 4, the graph showed that there was an inverse relationship between the average element minimum principal stresses and the Young's modulus of the plate. It was observed that there was a change in the gradient of the curve at the transition point in between 50 GPa to 100 GPa. When the Young's modulus was reduced to less than 50 GPa, the minimum principal stress increased rapidly in response to a further decrease in the Young's modulus.

In Part (2), in the CAD design file, the location and number of screw holes on plate can be adjusted to improve the fixation of plate to the bone as well as to minimise stress induced. Furthermore, the plate can be precisely contoured to the fracture model. Precise contouring to the fracture model can further improve plate fitting to the anatomy.

Figure 6:
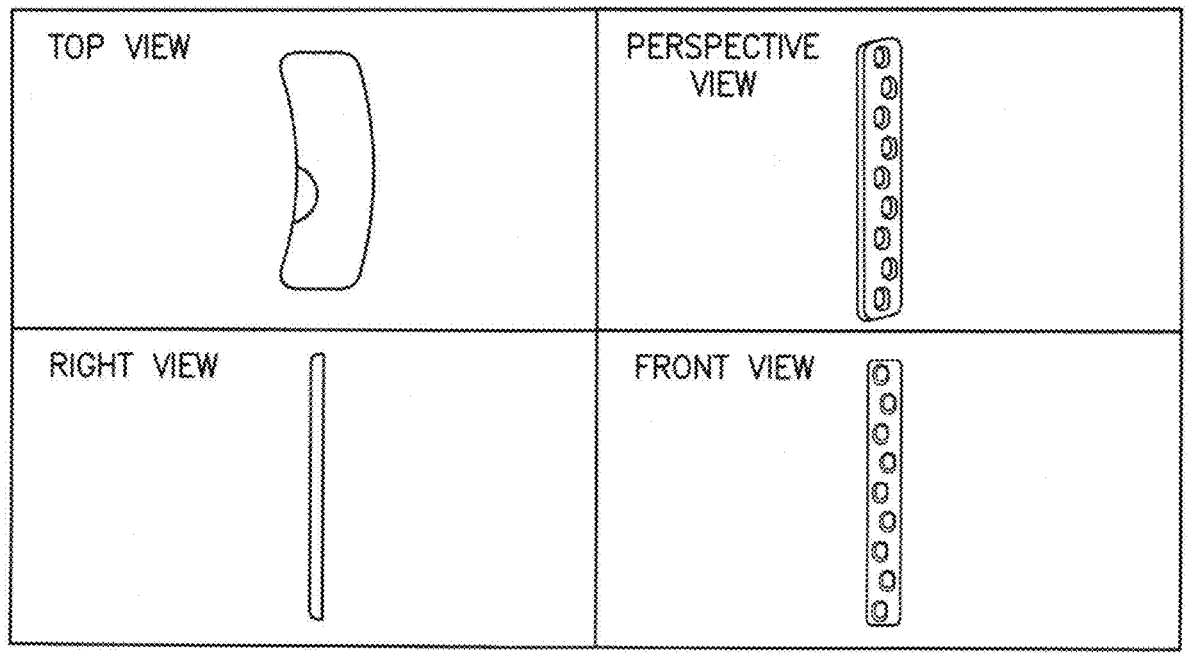
FIG. 6 shows (a) a cross-sectional view of a reference plate; (b) an illustration of design dimensions referring to a reference plate; (c) a primary customization to remove redundant screw holes and locate functional screw holes.
Figure 6:
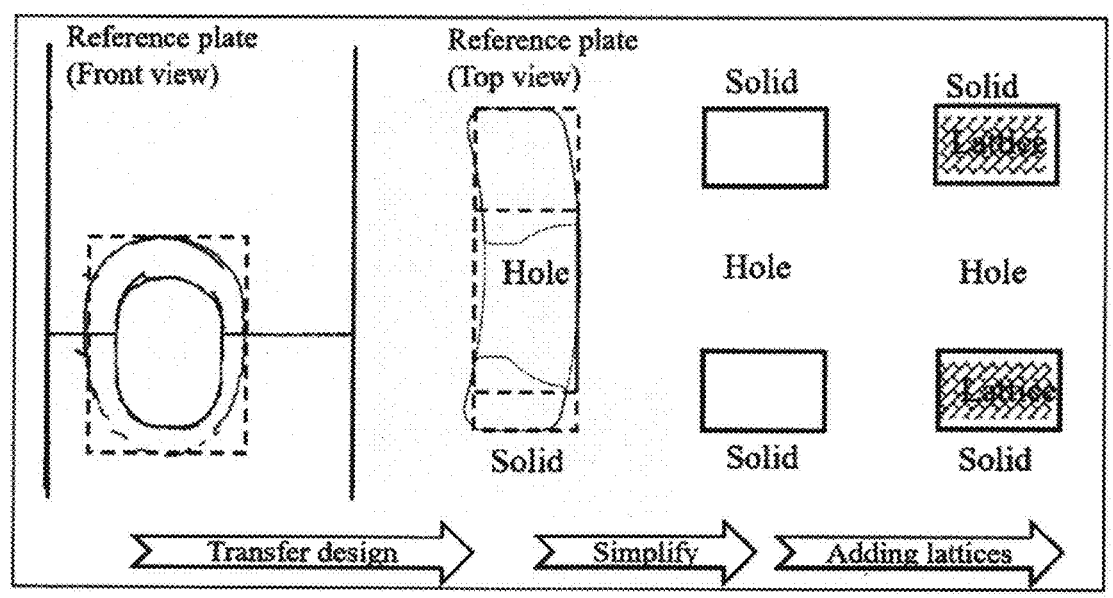
Figure 6:
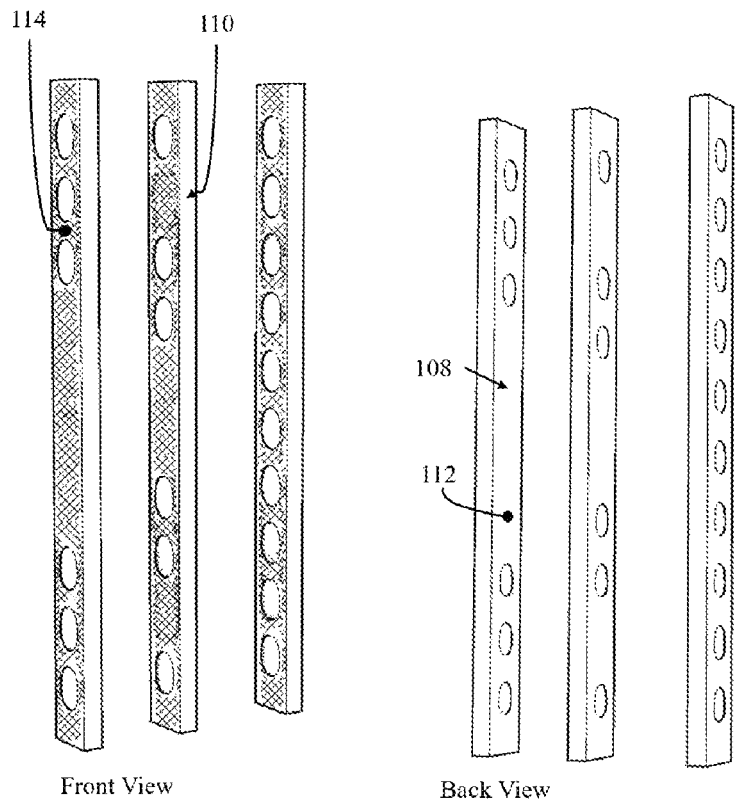
Figure 7:
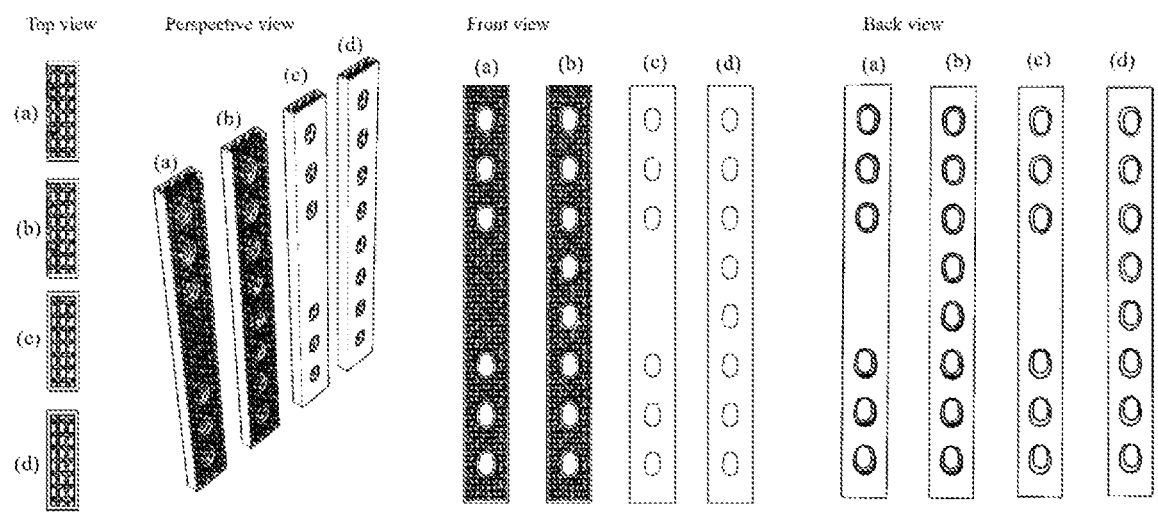
FIG. 7 illustrates a fully customized plate with removed redundant screw holes, and opened or closed plates to optimize the bending structural stiffness and structural modulus for each patient.

In Part (3), by selecting the internal lattices, features of the solid shell such as being fully closed or, alternatively, opened at the front, as well as the locations and numbers of functional screw holes, and the fracture fixation plate can be customized as shown in FIGS. 5 to 7.

In examples shown in FIGS. 5 to 7, the lattice structures were truss-based. In particular, three truss-based lattice structures were selected for bone plate applications. In FIG. 5a, the truss-based lattice structures were inspired from the truncated cube 126, dodecahedron structure 128, and pillar-octahedral lattice 130. In addition, five bio-inspired structures 132, 134, 136, 138 and 140 shown in FIG. 5b were tested.

To ensure accurate modelling of the plates and the ability to convert the modelled plate performed to the performance of the printed plate prototype, composite beam theory was used for calculation, with a correction factor obtained from high-resolution XCT scanning on the selective laser melting (SLM) prototypes as discussed below. In particular, composite beam theory was used to predict the modulus and bending structural stiffness of plate with optimized internal lattices.

In addition, using FEA, the principle stresses on plates were analysed when the flexure modulus of material was reduced. FIG. 4 suggests that a material with flexure modulus of around 50 GPa is preferred in bone plate applications, since further decrease in flexure modulus caused exponential increase in the stress. For present purposes, the flexure modulus of prototypes were varied from 56 GPa to 100 GPa, with bending structural stiffness (defined in ASTM F382) varied from $4.32 \times 10^6$ N-mm$^2$ to $13.44 \times 10^6$ N-mm$^2$.

Figure 8:
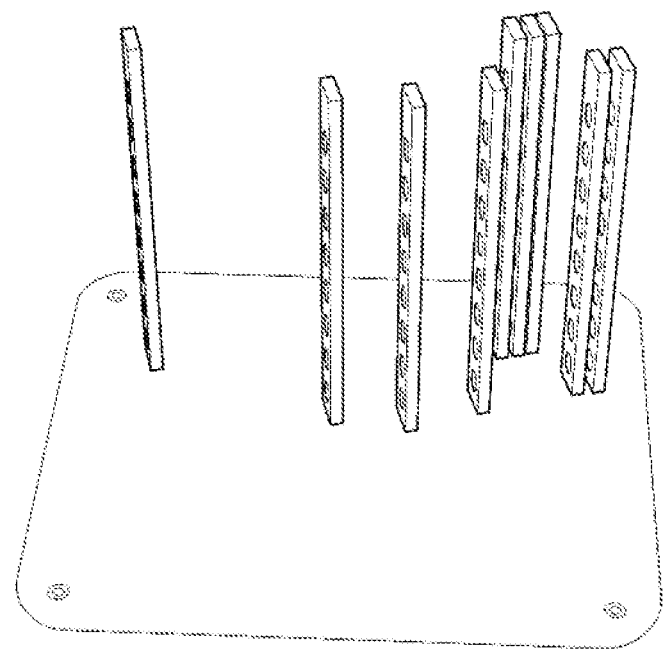
FIG. 8 comprising FIGS. 8(a) and (b), illustrates a design arrangement of plates for mass production—plates were arranged by orienting the length in the z-direction to enable mass production in additive manufacturing or 3-dimensional (3D) printing such as selective laser melting (SLM)
Figure 8:
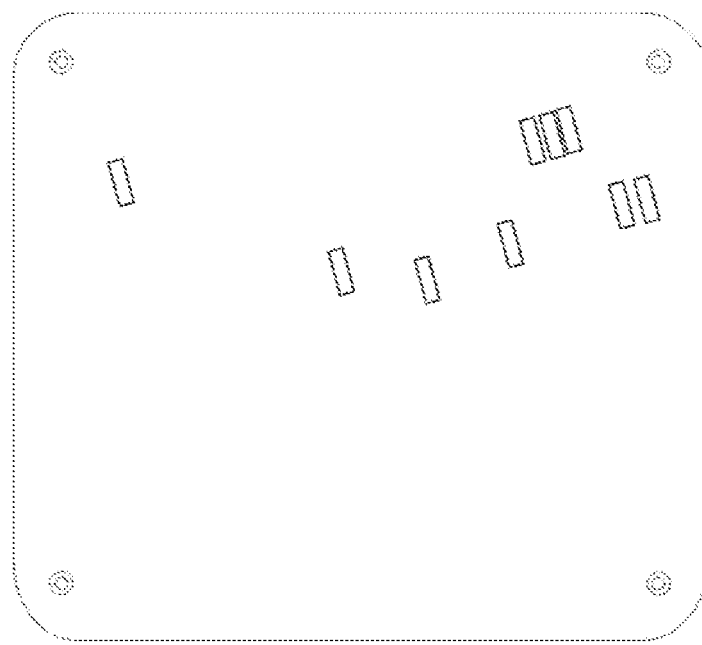

In experimentation, the plate designs were printed using SLM in commercially available metal printers. To facilitate mass production, plates were arranged by orienting the length in the z-direction as shown in FIG. 8. In this example, a few plates were semi-randomly spaced to examine the maximum distortions of parts in selective laser melting (SLM), as dense packaging can reduce part distortions due to bundle or array situation of adjacent plates. Printing parameters for the examples shown in FIGS. 5 to 7 are provided in Table 1 with the printing tolerances provided in Table 2.

TABLE 1

Printing parameters used in selective laser melting method when printing the designs in this invention.

| Printing Parameters | |
|---|---|
| 1) Laser Power | 200 W |
| 2) Scan Speed | 600 mm/second |
| 3) Hatch Distance | 0.06 mm |
| 4) Layer Thickness | 0.05 mm |
| 5) Laser Spot Size | 0.07 mm |
| 6) Laser exposure time | 50 ms |
| 7) Post Processing | Glass Beads Blasting |
| 9) powder size | 25 microns to 45 microns |

NOTE:
the printing parameters are provided by the equipment provider for general printing purposes.

TABLE 2

Printing tolerances measured using high resolution XCT scanning. Samples having features of solid shell and internal lattices were printed, with increasing aspect ratio of height\width (Z\X) and height\thickness (Z\Y).

| Z\X | Z\Y | $\Theta_{L-F}$ | $\Theta_{L-B}$ | $\Theta_{R-F}$ | $\Theta_{R-B}$ | $\Theta_{T-L}$ | $\Theta_{T-R}$ | $\Theta_{T-F}$ | $\Theta_{T-B}$ |
|---|---|---|---|---|---|---|---|---|---|
| 11:1 | 32:1 | 90.43 | 89.78 | 90.52 | 89.28 | 90.6 | 89.9 | 90.01 | 89.92 |
| 12:1 | 46:1 | 90.14 | 89.88 | 90.02 | 89.97 | 90.49 | 89.5 | 90.3 | 89.7 |
| 13:1 | 37:1 | 90.18 | 89.81 | 90.47 | 89.55 | 90.14 | 89.84 | 90.37 | 89.52 |
| 14:1 | 54:1 | 90.89 | 89.01 | 90.74 | 89.36 | 90.24 | 89.75 | 90.37 | 89.68 |
| 16:1 | 62:1 | 90.65 | 89.11 | 90.68 | 89.56 | 90.12 | 89.87 | 90.02 | 89.92 |

To ensure the dimensions of the plates were established to ensure performance of the plates matched that of the CAD designs, the flexure modulus and bending stiffness of the prototypes was established according to the following:

The bending stiffness of the bone plate was determined according to:

$$EI_e = \frac{(2h + 3a)Kh^2}{12} \quad (1)$$

where α is the centre span distance, h is the loading span distance, and K is the bending stiffness (Om).

The bending stiffness (EI) and modulus of plate were then predicted using composite beam theory when the external solid shell was selected based on the anatomy and fracture conditions, while the internal lattice was selected to tune the modulus and bending stiffness of the plate. In particular, the length, width and thickness of plate, the curvature of plate, as well as the relative position of screw holes on the plate, need to be customised for different fracture conditions. A broad range of lattices, freeform structures and porous structures, which could be uniform, non-uniform or anisotropic, provide different mechanical properties at different orientations, and could be used to tune the modulus and bending stiffness of the plate. If a cross-section of the implant is composed of a collection of basic shapes whose Young's moduli are known, along with the distances of the centroids to some reference point, then the parallel axis theorem can be used to calculate moment of inertia of the composite cross-section—i.e. the cross-section comprising the various basic shapes.

According to the parallel axis theorem, if replacing a less stiff material (lattice) with a stiffer material (solid), less of stiffer material is needed.

Figure 13:
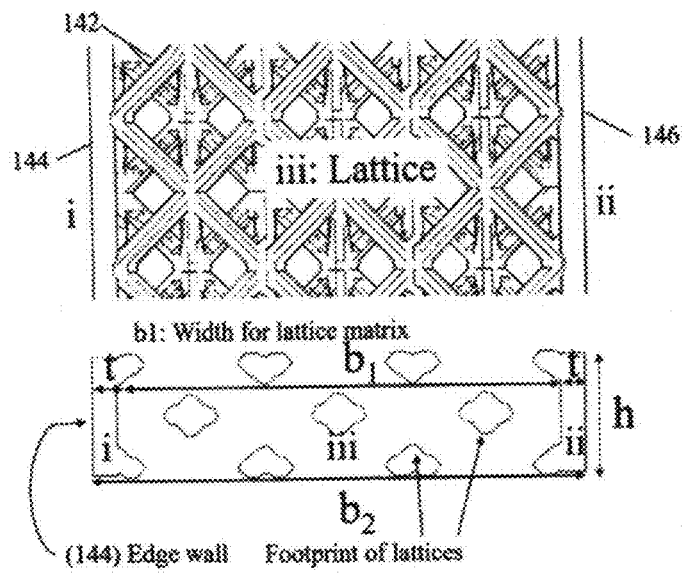
FIG. 13 is a schematic illustration of the primary design, with front view and cross-sectional view.

If n is assumed to be $E_{solid}/E_{lattice}$—where E is the Young's modulus—it follows that:

Fundamental equation for a solid:

$$I_s = \frac{bh^3}{12} \quad (2)$$

where $I_s$ is the moment of inertia for solid, b is the base and h is the thickness, where the direction of the base and thickness are indicated in FIG. 13.

This equation can be transformed to provide the result, according to beam theory, for a lattice ($I_l$):

$$I_l = \frac{bh^3}{12n} \quad (3)$$

In addition, the combined moment of inertia ($I_c$) for a composite beam is:

$$I_c = \Sigma(I_o + Ad^2) \quad (4)$$

in which $I_0$ is the moment of inertia for sub-section of the composite beam with area of $A_i$; $d=(y_i-\bar{y})$, $y_i$ is the vertical centroid for the sub-section of the composite beam with the area of $A_i$, and $\bar{y}$ is the vertical centroid of the composite beam determined according to:

$$\bar{y} = \frac{\sum y_i A_i}{\sum A_i} \quad (5)$$

Figure 16:
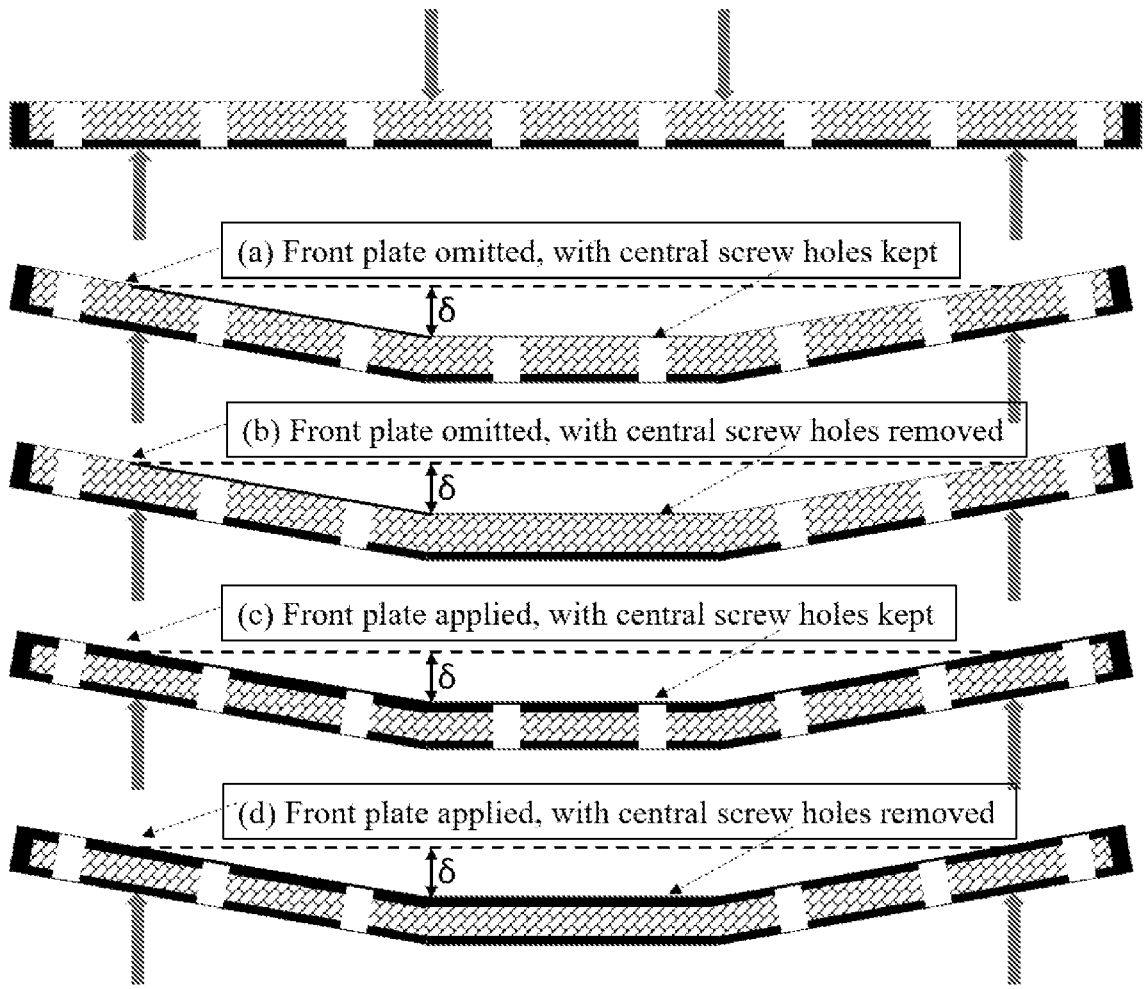
FIG. 16 comprises Illustrations of bending structural stiffness calculations when tested under setup configuration defined in ASTM F382.

For the flexure modulus ($E_f$) of a material with solid shell and internal lattices: it is assumed that the strain (ε) is kept consistent for both of solid and lattices during bending deformation (FIG. 16).

$$\sigma = E_f * \varepsilon \quad (6)$$

$$\sigma = F/A \quad (7)$$

where σ is the stress, F is a force applied to the material and A is the area over which the force is acting on.

Combining equations (6) and (7) yields:

$$E_f = \frac{A_s E_s + A_l E_l}{A_{total}} \quad (8)$$
$$= \frac{2t \times E_s + b_1 \times E_l}{b_1 + 2t}$$
$$= \left(\frac{2t}{b_1 + 2t}\right) \times E_s \times \left(1 + \left(\frac{b_1}{2t}\right)\frac{E_l}{E_s}\right)$$

Where, $A_s$ is the cross-section area of the solid, $A_l$ is the cross-section area of the space occupied by lattices, and $A_{total}$ is the total cross-section area of the composite beam; $E_s$ is the modulus of solid material, $E_l$ is the modulus of the lattices; $b_1$ is the base of the space occupied by lattices and t is the thickness of the side wall indicated in FIG. 13.

Assumption 1: it is a common challenge to calculate the mechanical behaviour of anisotropic lattices in light-weight structure applications. To simplify the calculations, we have constrained a block of repeating units (lattice matrix) within a solid shell, and treated the lattice matrix as a one-piece material with uniform mechanical properties in the specific loading direction tested. This assumption can be extended from lattice matrices to uniform or non-uniform freeform structures and porous structures, to test the mechanical performances in a specified orientation.

Assumption 2: the bending stiffness of lattice matrix and prototypes were tested under setup configuration defined by the ASTM F382 standard, which is specially used for bone plate testing.

Assumption 3: from HRXCT scanning measurements, the thin wall (i.e. solid shell) was over-printed by 14% while the outside contour dimensions remained unchanged. Meanwhile, the space for internal lattice matrix was reduced to compensate for the over printing of thin wall, with over-printing extending inwardly. Therefore, the correction factor of dimension was defined as 14% inward overprinting for solid shell when using the printing parameters and materials demonstrated herein. By changing the processing parameters, materials and designs, the correction factor may need to be re-calculated.

The calculated bending stiffness of prototypes using dimensions from the original design file and corrected values with correction factors applied have been compared, where the latter is closer to results from bending tests. If a different laser of printing strategy is used, the correction factor for dimensions may need to be adjusted.

Three steps were used to establish a prediction of bending stiffness of bone plate prototypes using design parameters.

In step 1, implants with a lattice matrix 142 reinforced by two thin walls 144,146 (FIG. 13) were printed to calculate the flexure modulus of the lattices. The lattice matrix was treated as one uniform material (Assumption 1). Dimensions of printed prototypes were measured using high-resolution XCT scanning to define the correction factors for use in calculations when parts are going to be fabricated in the AM system tested (Assumption 3).

In step 2, the same lattice matrices were reinforced by three side walls, i.e. a thin back plate and sidewalls along the edges (FIG. 14) to examine the accuracy of the equations in predicting bending stiffness (EI), and to fine tune the correlation or correction factors developed from step 1. After measuring and tuning the correction factors for solid shell and internal lattice matrix using HRXCT, corrections were applied to the dimensions of shell and internal lattice matrix in calculation of bending stiffness of plate, to account for the discrepancy between the designed dimensions and the as-printed dimensions. For each additive manufacturing system prepared to fabricate the plates, the correction factor can be determined using HRXCT with a few test printings, then the specific correction factor can be used to improve the accuracy of prediction of mechanical performance for plates.

In step 3, the lattice matrix was used to replace the internal solid core of a bone plate, and the corresponding predictions of the bending stiffness (EI) of the prototypes were close to the tested values.

The basis for these steps is set out below:

Step 1—Primary design: lattices were reinforced by two side walls along the edge (For example, Truss-3)—see FIG. 13.

Symmetrical structure along the thickness (h) orientation:

$d = 0$ $$I_f = \sum (I_o + Ad^2)$$
$$= \sum I_o$$
$$= I_i + I_{ii} + I_{iii}$$
$$= \left(2 \times \frac{th^3}{12}\right) + \frac{b_1 h^3}{12n}$$

$$E_f = \frac{A_s E_s + A_l E_l}{A_{total}}$$
$$= \frac{2t \times E_s + b_1 \times E_l}{b_1 + 2t}$$
$$= \left(\frac{2t}{b_1 + 2t}\right) \times E_s \times \left(1 + \left(\frac{b_1}{2t}\right)\frac{E_l}{E_s}\right)$$

In this primary design, d=0 means the centroid of solid side walls is equal to the centroid of lattice matrix; $I_f$ and $E_f$ represent the flexure moment of inertial and flexure Young's modulus of the structure composed of side walls and lattice matrix indicated in FIG. 13.

From equations (2) and (4):

$$I_f = \frac{I_s E_s + I_l E_l}{E_s} = \frac{2t \times (h)^3}{12} \times \left(1 + \left(\frac{b_1}{2t}\right)\frac{E_l}{E_s}\right)$$

$E_f I_f = EI_e$ (obtained from destructive test of this bending bar according to ASTM-F382), the term $EI_e$ indicates elastic bending stiffness, i.e. no plastic deformation for terms b, t, and h was assumed.

In the examples tested as described herein, parameters used in design were (FIG. 13):

t=0.7 mm;
$h_1$=3.4 mm;
$b_1$=12.75 mm;
$b_2$=14.15 mm.

The dimensions of parts were measured using high resolution XCT scanning, and the estimated average values from prototypes were:

t=0.8 mm;
$h_1$=3.4 mm;
$b_1$=12.55 mm;
$b_2$=14.15 mm;

$E_s$=140000 MPa (from tensile and bending test of solid bar from additive manufacturing). Therefore:

$$E_f \times I_f = \left(\frac{2t}{b_1 + 2t}\right) \times \frac{2t \times (h)^3}{12} \times E_s \times \left[1 + \left(\frac{b_1}{2t}\right)\frac{E_l}{E_s}\right]^2 \quad (9)$$

Calculating the modulus of the lattices using equation (9), the lattices produced the results set out in Table 3.

TABLE 3

The experimental bending stiffness (EI) and calculated modulus of lattices.

| | $EI_e$ (N·mm²) | $E_{lattice}$ (MPa) |
|---|---|---|
| Truss 1 | $1.367 \times 10^6$ | 54600 |
| Truss 2 | $1.162 \times 10^6$ | 48943 |
| Truss 3 | $0.786 \times 10^6$ | 37093 |
| Bioinspired 1 | $0.639 \times 10^6$ | 31704 |
| Bioinspired 2 | $0.524 \times 10^6$ | 27032 |
| Bioinspired 3 | $0.554 \times 10^6$ | 28523 |
| Bioinspired 4 | $0.529 \times 10^6$ | 27225 |
| Bioinspired 5 | $0.639 \times 10^6$ | 31704 |

Figure 14:
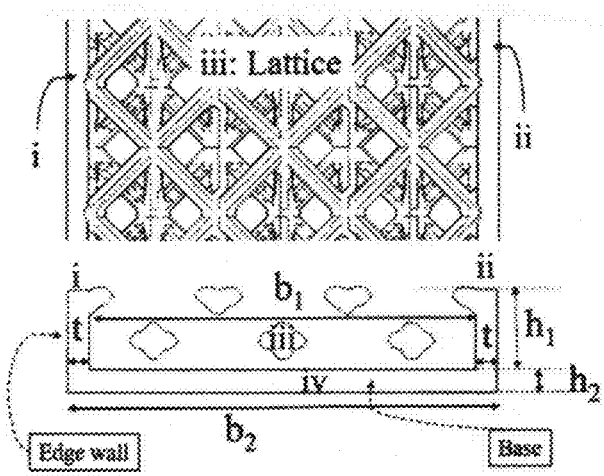
FIG. 14 is a schematic illustration of the transitional design, with front view and cross-sectional view.

Step 2—Transitional design: lattices were reinforced by solid edges and back (For example, Truss-3)—see FIG. 14.

Modifying the above equations to fit the structure shown in FIG. 14 yields the equations shown in Table 4.

TABLE 4

Equations for different parts based on composite beam theory.

| parts | $I_o$ (mm⁴) | $A_i$ | $y_i$ | d |
|---|---|---|---|---|
| i | $\frac{th_1^3}{12}$ | $th_1$ | $h_1/2$ | $\frac{h_1}{2} - \bar{y}$ |
| ii | $\frac{th_1^3}{12}$ | $th_1$ | $h_1/2$ | $\frac{h_1}{2} - \bar{y}$ |
| iii | $\frac{b_1 h_1^3}{12n}$ | $(b_1 h_1)/n$ | $h_1/2$ | $\frac{h_1}{2} - \bar{y}$ |
| iv | $\frac{b_2 h_2^3}{12}$ | $b_2 h_2$ | $h_1 + (h_2/2)$ | $\left[h_1 + \frac{h_2}{2}\right] - \bar{y}$ |

In addition:

$I_f = \Sigma(I_o A d^2)$ where $d = y_i - \bar{y}$, where $\bar{y}$ is the vertical centroid of the composite beam calculated according to:

$$\bar{y} = \frac{\sum \bar{y}_i A_i}{\sum A_i}$$

By applying the modulus of lattices calculated from the primary design according to Step 1 (FIG. 13), the $EI_e$ (bending stiffness) of the transitional designs were calculated and compared to the experimental values.

Figure 9:
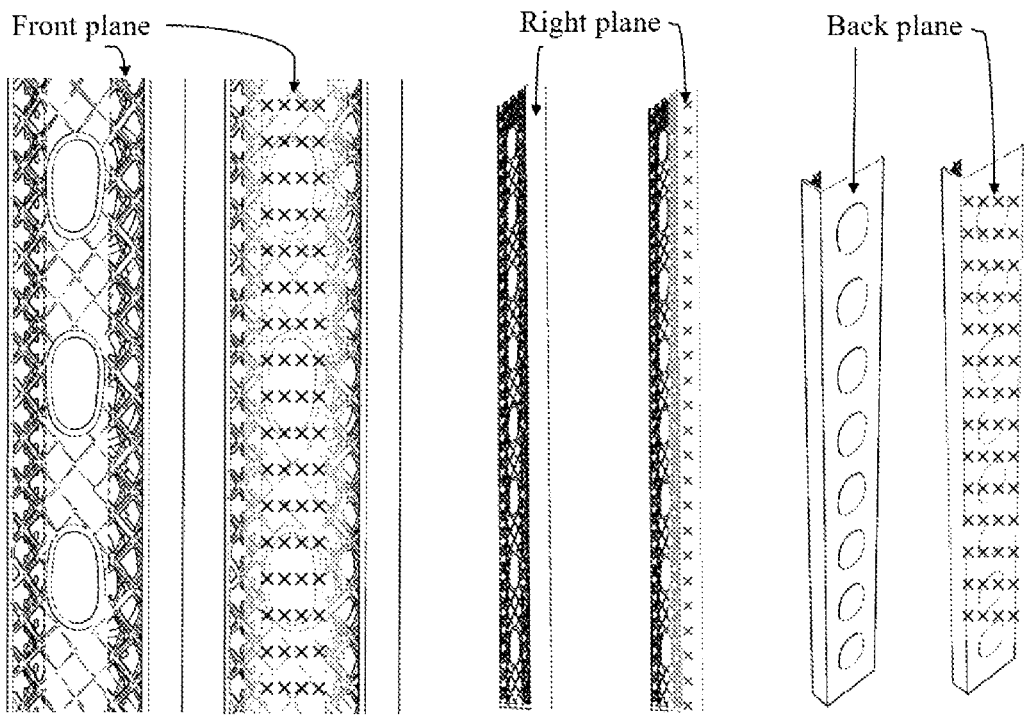
FIG. 9 illustrates (a) the calculation of printing tolerances determined using high resolution X-Ray computer tomography (HRXCT) scanning; (b) the arrangement of axes within a 3D printer; and (3) defining of bounding box in measuring the angles between intersection planes (results shown in Table 2)
Figure 9:
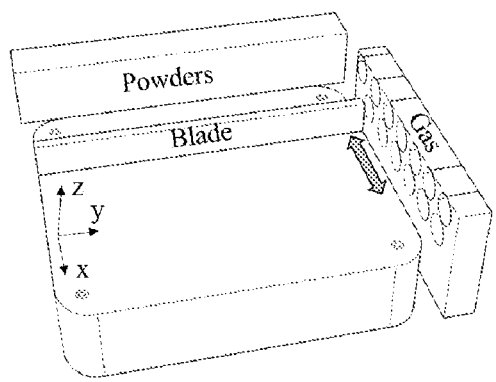
Figure 9:
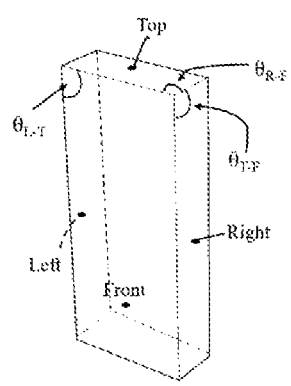
Figure 10:
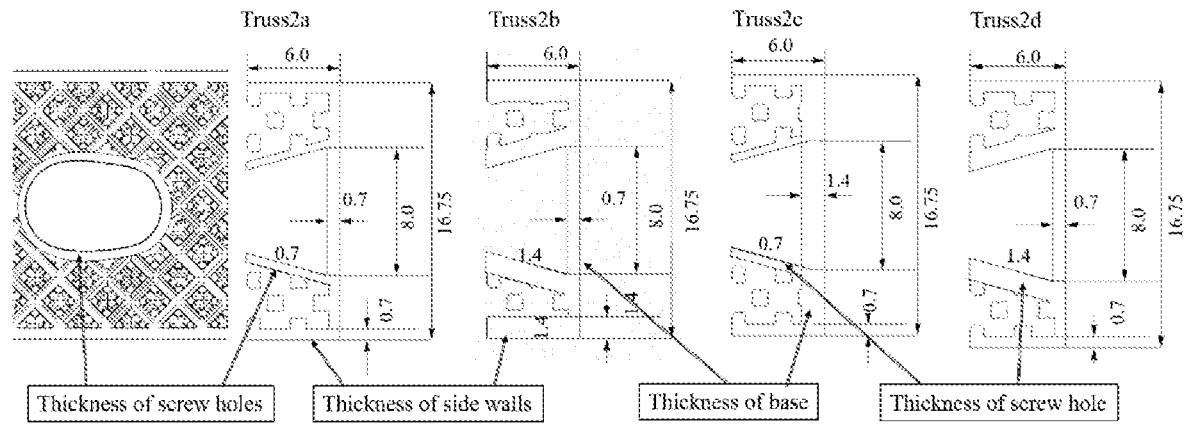
FIG. 10 shows example modelled plate prototypes with a cross-sectional view at the screw hole as indicated on the left.
Figure 11:
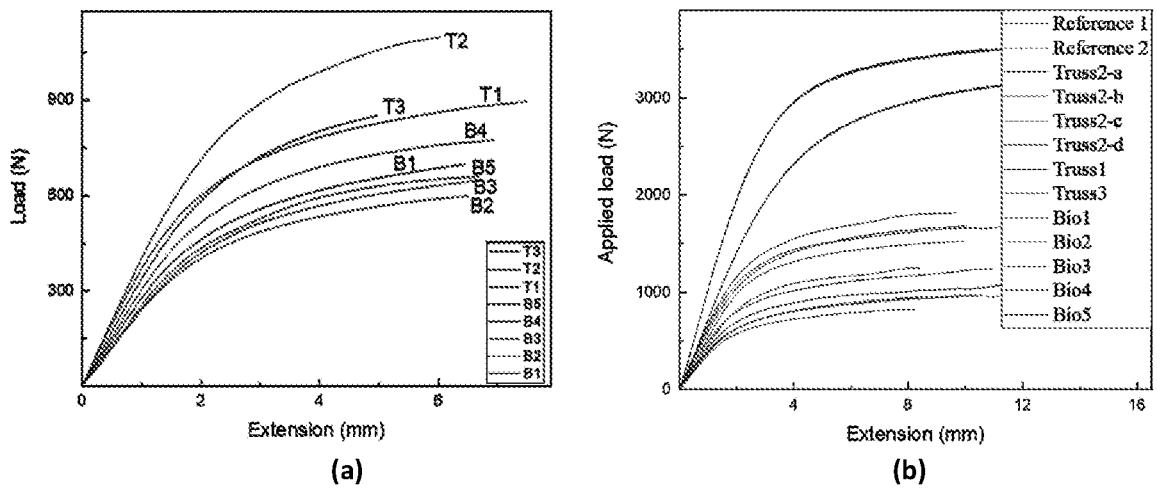
FIG. 11 shows a Load-Extension curve of customized bone plate, including (a) design-1 having thickness of 5.2 mm and width of 16.75 mm, with different internal lattices; (b) design-2 having thickness of 6.0 mm and width of 16.75 mm with different internal lattices; (c) design-3 having thickness of 5.2 mm and width of 16.25 mm, with front opened and fully closed solid shells, and with two central screw holes kept and removed, wherein T3 and B3 internal lattices were applied separately.
Figure 12:
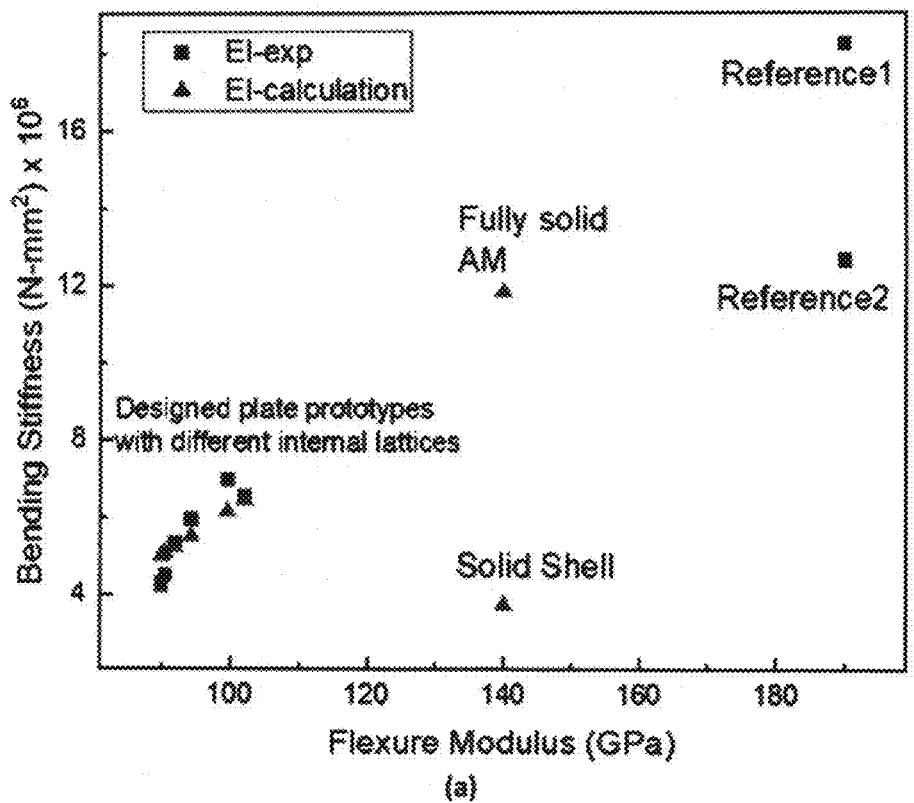
FIG. 12 compares the bending stiffness of bone plate prototypes with reference plates, including (a) prototype for Design-1 having thickness of 5.2 mm and width of 16.75 mm; (b) for design-2 having thickness of 6.0 mm and width of 16.75 mm; (c) for design-3 having thickness of 5.2 mm and width of 16.25 mm with varying design features of solid shell and different number of screw holes; and (d) a summary of the bending stiffness of prototypes that were printed and tested.
Figure 12:
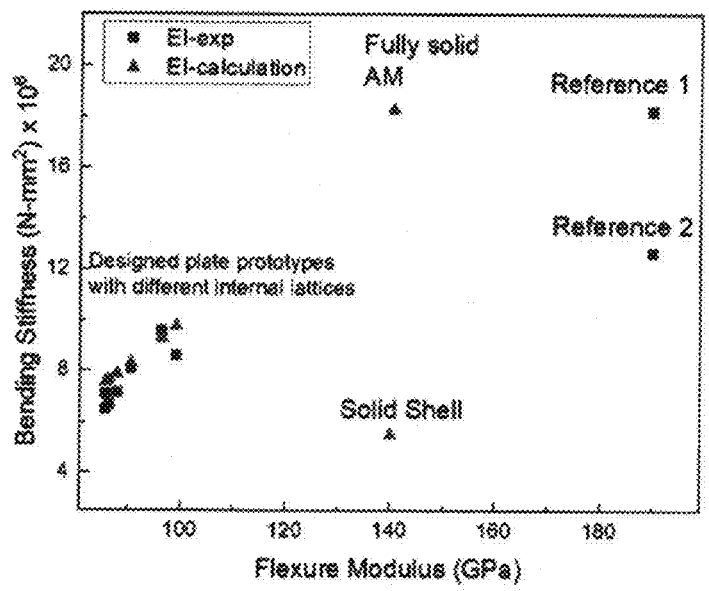
Figure 12:
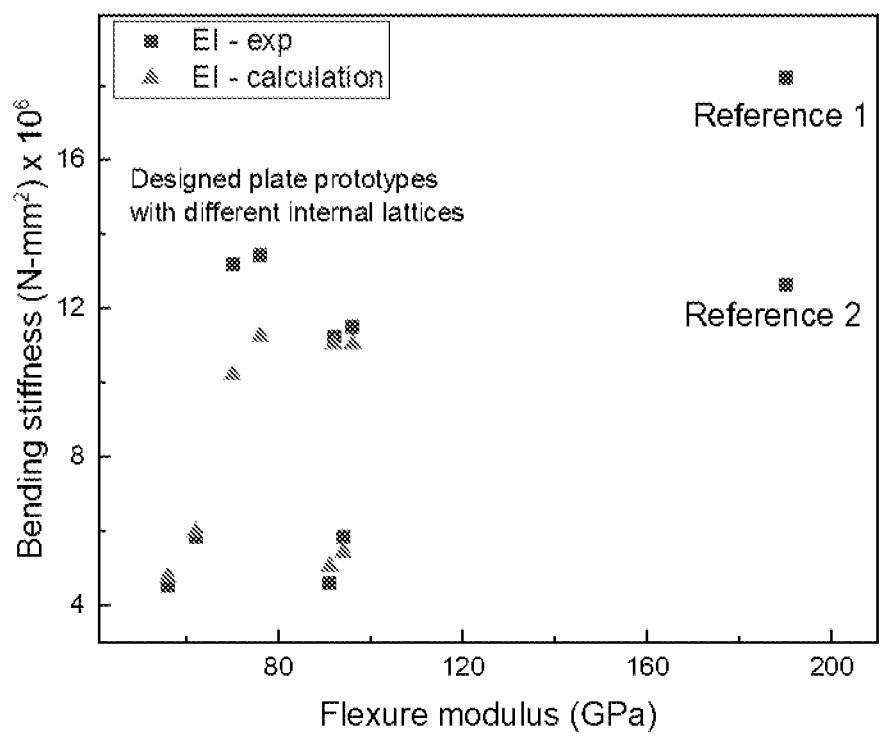
Figure 12:
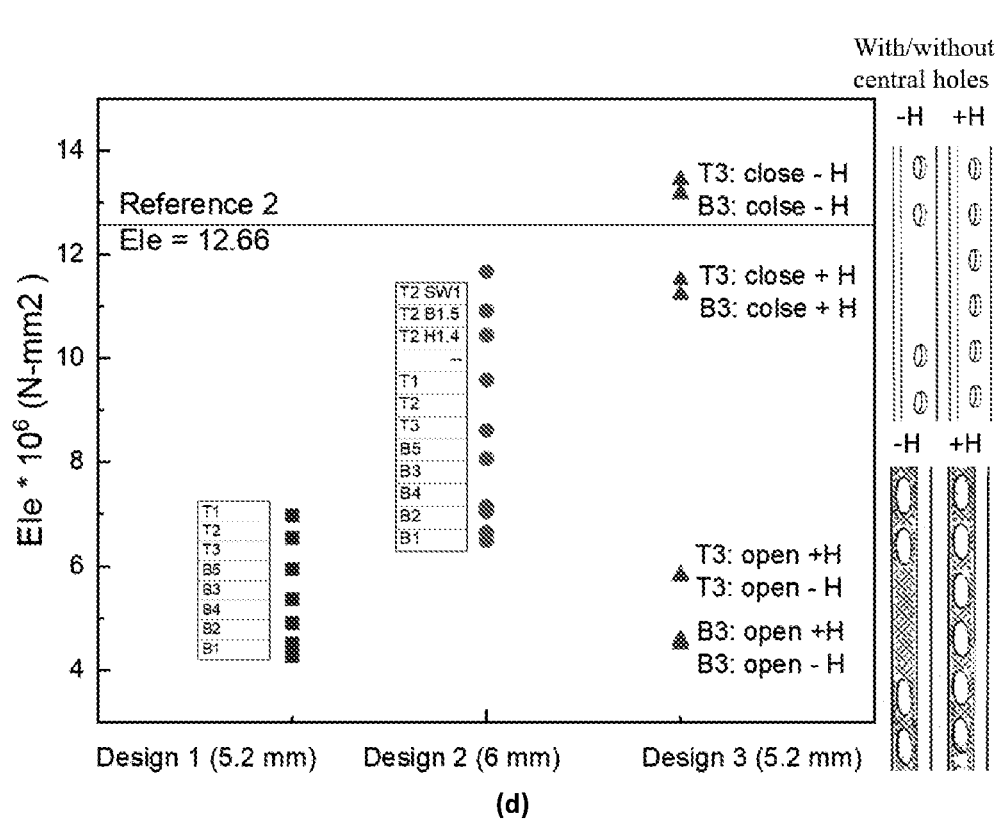

From HRXCT measurement on the printing (FIG. 9), correction factor of 14% was applied to the thickness of thin walls inwardly, while the contouring dimensions remained unchanged. The variance of calculations using designed and corrected values were compared in Table 5(a) and 5(b), where the prediction using corrected dimensions were closer to the tested values.

TABLE 5(a)

The experimental and calculated bending stiffness ($EI_e$) of plates from additive manufacturing, dimensions from original designs were used.

| | $E_{lattice}$ (MPa) | $EI_e$ from calculation (designed values) (N/mm²) | $EI_e$ from Experiment (N/mm²) | Discrepancy (%) 100* ($EI_{exp}$ − $EI_{cal}$)/$EI_{exp}$ |
|---|---|---|---|---|
| Truss1 | 54600 | 2.88 × 10⁶ | 2.39 × 10⁶ | 20.5% |
| Truss2 | 48943 | 2.59 × 10⁶ | 2.96 × 10⁶ | 12.5% |
| Truss3 | 37093 | 2.02 × 10⁶ | 2.26 × 10⁶ | 10.6% |
| Bioinspired 1 | 31704 | 1.78 × 10⁶ | 1.99 × 10⁶ | 10.6% |
| Bioinspired 2 | 27032 | 1.57 × 10⁶ | 1.84 × 10⁶ | 14.7% |
| Bioinspired 3 | 28523 | 1.61 × 10⁶ | 1.76 × 10⁶ | 8.5% |
| Bioinspired 4 | 27225 | 1.58 × 10⁶ | 1.87 × 10⁶ | 15.5% |
| Bioinspired 5 | 31704 | 1.78 × 10⁶ | 1.98 × 10⁶ | 10.1% |

TABLE 5

(b) The experimental and calculated bending stiffness ($EI_e$) of plates from additive manufacturing, and dimensions of corrected values were used.

| | $E_{lattice}$ (MPa) | $EI_e$ from calculation (corrected values) (N/mm²) | $EI_e$ from Experiment (N/mm²) | Discrepancy (%) 100* ($EI_{exp}$ − $EI_{cal}$)/$EI_{exp}$ |
|---|---|---|---|---|
| Truss1 | 54600 | 3.04 × 10⁶ | 2.39 × 10⁶ | 27.2% |
| Truss2 | 48943 | 2.75 × 10⁶ | 2.96 × 10⁶ | 7.1% |
| Truss3 | 37093 | 2.18 × 10⁶ | 2.26 × 10⁶ | 3.5% |
| Bioinspired 1 | 31704 | 1.94 × 10⁶ | 1.99 × 10⁶ | 2.5% |
| Bioinspired 2 | 27032 | 1.73 × 10⁶ | 1.84 × 10⁶ | 6.0% |
| Bioinspired 3 | 28523 | 1.78 × 10⁶ | 1.76 × 10⁶ | 1.1% |
| Bioinspired 4 | 27225 | 1.74 × 10⁶ | 1.87 × 10⁶ | 7.0% |
| Bioinspired 5 | 31704 | 1.94 × 10⁶ | 1.98 × 10⁶ | 2.0% |

Step 3—Bone Plate Prototypes

As discussed above, in Step 3 the lattice matrix was used to replace the internal solid core of a bone plate. The corresponding predictions of the bending stiffness ($EI_e$) of the prototypes were found to be close to the tested values.

In the following discussion, Feature I involves lattices being embedded in opened solid shell comprising solid edges and back, Feature II involves lattices being enclosed in fully closed solid shell and Feature III involves adjusting the location and number of screw holes. Those features can be further varied according to the anatomy and fracture conditions of patients.

Figure 2:
FIG. 2 illustrates the FEA analysis of stress distribution under loading of the body weight, (a) on standard narrow bone plate for use on a fracture of 42A1 Type, 1 mm gap; (b) on modified bone plate with two central redundant holes removed for use on a fracture of 42A1 Type, 1 mm gap.
Figure 2:
Figure 3:
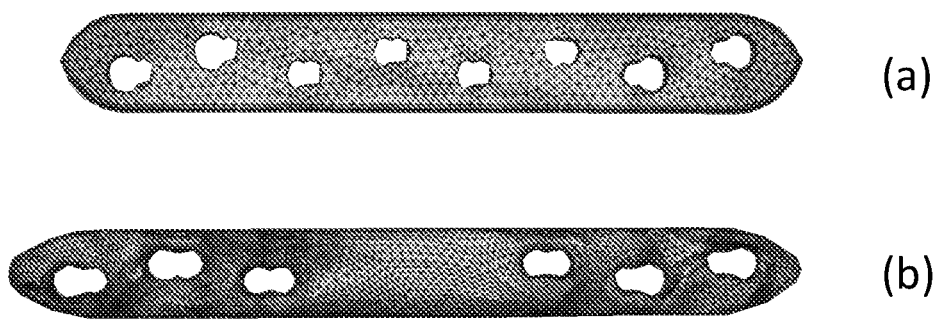
FIG. 3 shows FEA analysis of stress distribution under loading of the body weight, (a) on standard broad bone plate, (b) on modified bone plate with two central redundant holes removed.
Figure 4:
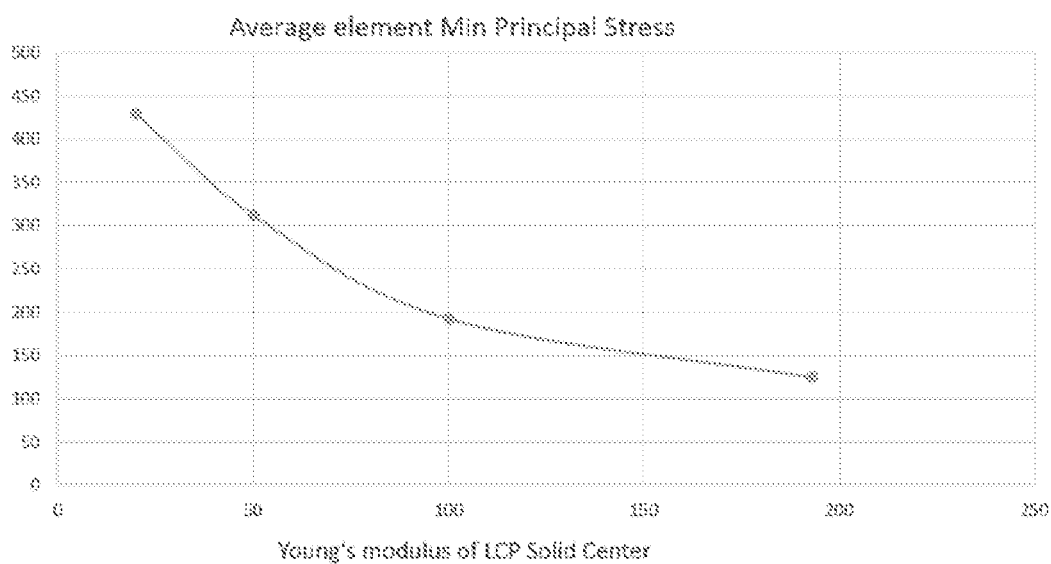
FIG. 4 shows changing of minimum principal stress when the young's modulus of material was decreased from 193 GPa to 20 GPa.
Figure 15:
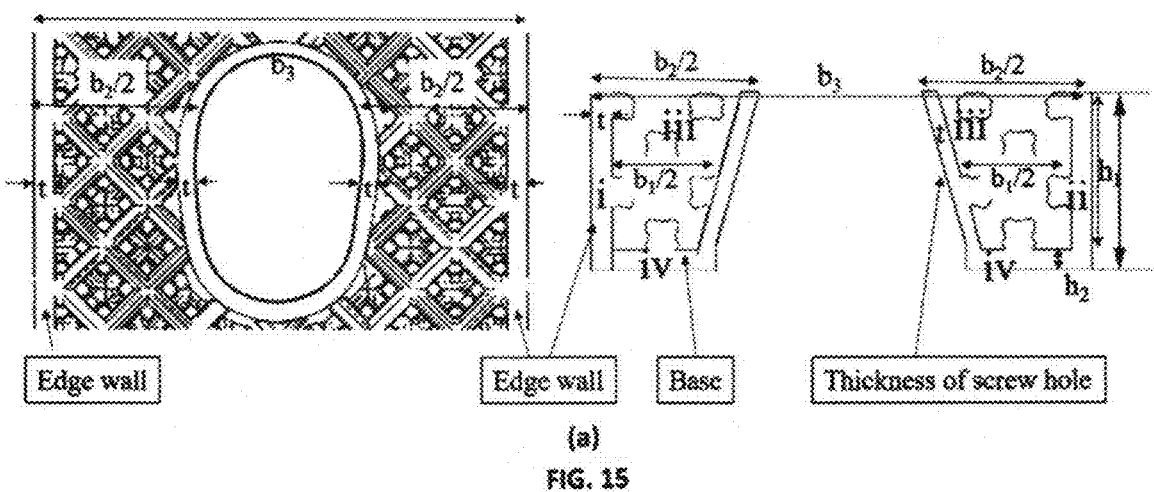
FIG. 15 shows (a) a schematic illustration of the bone prototype with optimized internal lattices, with front view and cross-sectional view at hole region; (b) an illustration of third design, lattices were constrained within a closed surface; and (c) the further simplified cross-section of bone plate prototype and corresponding dimensions used in calculations.
Figure 15:
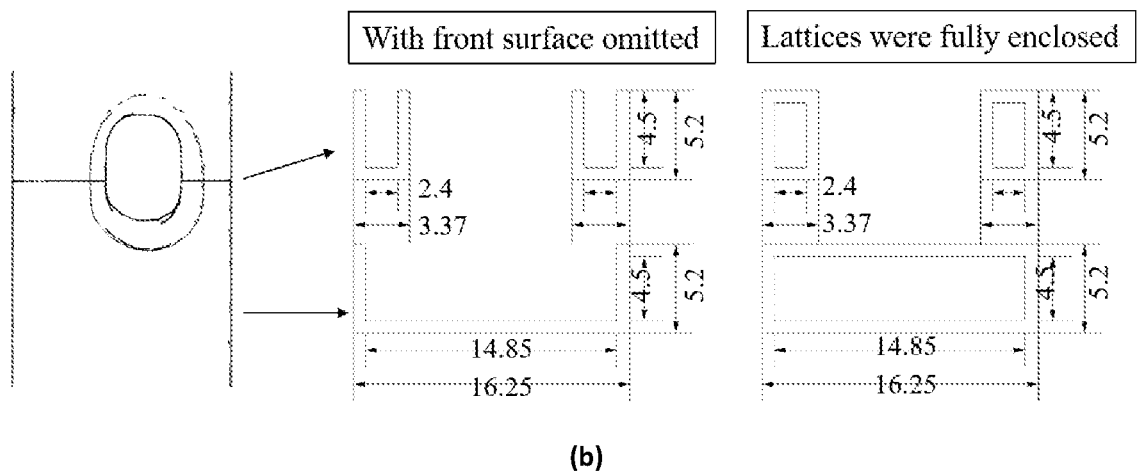
Figure 15:
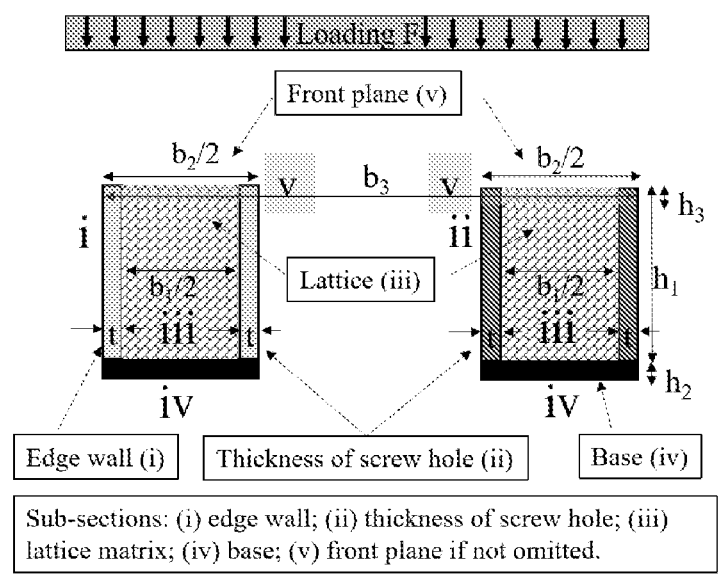

Since regions with screw holes are the weakest regions on plate as shown in FEA study in FIGS. 2 and 3, the cross-section of region with maximum screw hole circumference, which is referring to the location on the base of the plate where the screw holes have the maximum diameter $b_3$, was taken for bending stiffness calculations as indicated in FIG. 15 in which an orthopaedic trauma plate is shown with front plate omitted and in which t indicates wall thickness, 111 indicates edge walls, b indicates the base, $b_1$ indicates the thickness of the base at half height $h_1$ of the lattice, $h_2$ indicates the thickness of the base, and $b_2$ indicates the width opposite the base. Roman numbers (i, ii, iii, iv, v) indicate the sub-section or sub-part composing the "composite beam", which have been treated as single material unit having individual inertia and Young's modulus (summarized in Table 7a and 7b). Therefore, those values were used to calculate the composite beam bending stiffness using composite beam theory.

To further widen the mechanical tolerances of new bone plate designs, three design batches of bone plates having different dimensions and features were printed and tested.

The first design batch of bone plate had a shell having thickness of 5.2 mm, and width of 16.75 mm, and Feature I was applied as shown in FIG. 15(a). The second design batch of bone plate had a shell having thickness of 6.0 mm, and width of 16.75 mm, Feature II was applied as shown in FIG. 15(a). The third design of bone plate had a shell having thickness of 5.2 mm, and width of 16.25 mm as shown in FIG. 15(b). In this batch of design, features I, II, and III were all applied. Three design batches thus had different dimensions and the Features I, II and III were tested with the three truss-based internal lattices and five bioinspired lattices shown in FIGS. 5a and 5b.

By applying the modulus of lattices calculated from primary and transitional designs, the $EI_e$ (bending stiffness) of bone plate prototypes were calculated and compared to the experimental values. In bone plate calculation, correction factor of 14% on the thin wall was applied using the additive manufacturing system tested, while the contouring dimensions have been kept unchanged. The design and corrected dimensions using correction factor from HRXCT measurements are reflected in Table 6.

TABLE 6

Comparing of the designed dimensions and corrected dimensions from SLM printed part.

| Parameters defined in FIG. 14 | Design batch 1 Feature I Design/Corrected | Design batch 2 Feature I Design/Corrected | Design batch 3 Features I, II, III Design/Corrected |
|---|---|---|---|
| t (mm) | 0.7/0.8 | 0.7/0.8 | 0.7/0.8 |
| $h_1$ (mm) | 4.5/4.4 | 5.3/5.2 | 4.5/4.4 |
| $h_2$ (mm) | 0.7/0.8 | 0.7/0.8 | 0.7/0.8 |
| $h_3$ (mm) | 0/0 | 0/0 | 0/0 (no top, open shell) 0.7/0.8 (with top, closed shell) |
| $b_1$ (mm) | 3.93/4.03 | 3.93/4.03 | 3.93/3.53 (with hole) 14.85/14.65 (remove hole) |
| $b_2$ (mm) | 7.23/7.23 | 7.23/7.23 | 6.73/6.73 (with hole) 16.25/16.25 (remove hole) |
| $b_3$ (mm) | 16.75/16.75 | 16.75/16.75 | 16.25/16.25 |

In addition, experiments were established based on the retention and removal of central screw holes, the equations for which are set out in Tables 7a and 7b respectively.

TABLE 7(a)

Equations for different parts based on composite beam theory, with central screw holes kept in prototypes.

| parts | $I_o$ (mm⁴) | $A_i$ | $y_i$ |
|---|---|---|---|
| i | $[2t \times (h_1 - h_3)^3]/12$ | $2t \times (h_1 - h_3)$ | $(h_1 + h_3)/2$ |
| ii | $[2t \times (h_1 - h_3)^3]/12$ | $2t \times (h_1 - h_3)$ | $(h_1 + h_3)/2$ |
| iii | $[(b_2 - 4t) \times (h_1 - h_3)^3]/(12n)$ | $[b_1 \times (h_1 - h_3)]/n$ | $(h_1 + h_3)/2$ |
| iv | $[b_2 \times (h_2)^3]/12$ | $b_2 \times h_2$ | $h_1 + (h_2/2)$ |
| v | $[b_2 \times (h_3)^3]/12$ | $b_2 \times h_3$ | $h_3/2$ |

TABLE 7(b)

Equations for different parts based on composite beam theory, with central screw holes removed in prototypes.

| parts | $I_o$ (mm$^4$) | $A_i$ | $y_i$ |
|---|---|---|---|
| i | $[t \times (h_1 - h_3)^3]/12$ | $t \times (h_1 - h_3)$ | $(h_1 + h_3)/2$ |
| ii | $[t \times (h_1 - h_3)^3]/12$ | $t \times (h_1 - h_3)$ | $(h_1 + h_3)/2$ |
| iii | $[(b_3 - 2t) \times (h_1 - h_3)^3]/(12n)$ | $[(b_3 - 2t) \times (h_1 - h_3)]/n$ | $(h_1 + h_3)/2$ |
| iv | $[b_3 \times (h_2)^3]/12$ | $b_3 \times h_2$ | $h_1 + (h_2/2)$ |
| v | $[b_3 \times (h_3)^3]/12$ | $b_3 \times h_3$ | $h_3/2$ |

In Table 8, the predicted and experimental values of bending structural stiffness were compared, with good tolerances for majority of prototypes.

TABLE 8

The experimental and calculated bending structural stiffness (EI) of different bone plate prototypes from additive manufacturing.

| | E flexural (GPa) | $EI_{cal}$ (N-mm$^2$) | $EI_{exp}$ (N-mm$^2$) | Discrepancy (%) = ($EI_{exp}$ − $EI_{cal}$)/$EI_{exp}$ |
|---|---|---|---|---|
| Reference 1 | 190 | | 18.24 × 10$^6$ | |
| Reference 2 | 190 | | 12.66 × 10$^6$ | |
| Feature 1 | | | | |
| Design 1 (truss 1) | 102.1 | 6.46 × 10$^6$ | 6.55 × 10$^5$ | 1.4% |
| Design 1 (truss 2) | 99.6 | 6.15 × 10$^6$ | 6.98 × 10$^5$ | 11.9% |
| Design 1 (truss 3) | 94.3 | 5.53 × 10$^6$ | 5.95 × 10$^6$ | 7.1% |
| Design 1 (bioinspired 1) | 91.9 | 5.25 × 10$^6$ | 4.9 × 10$^5$ | 7.1% |
| Design 1 (bioinspired 2) | 89.8 | 5.02 × 10$^6$ | 4.27 × 10$^6$ | 17.6% |
| Design 1 (bioinspired 3) | 90.5 | 5.09 × 10$^6$ | 4.52 × 10$^6$ | 12.6% |
| Design 1 (bioinspired 4) | 89.9 | 5.03 × 10$^6$ | 4.32 × 10$^6$ | 16.4% |
| Design 1 (bioinspired 5) | 91.9 | 5.25 × 10$^6$ | 5.36 × 10$^6$ | 2.1% |
| Feature 1 | | | | |
| Design 2 (truss 1) | 99.2 | 9.77 × 10$^6$ | 8.61 × 10$^6$ | 13.5% |
| Design 2 (truss 2) | 96.5 | 9.29 × 10$^5$ | 9.58 × 10$^6$ | 3.0% |
| Design 2 (truss 3) | 90.7 | 8.31 × 10$^6$ | 8.07 × 10$^6$ | 3.0% |
| Design 2 (bioinspired 1) | 88.1 | 7.89 × 10$^6$ | 7.05 × 10$^6$ | 11.9% |
| Design 2 (bioinspired 2) | 85.9 | 7.52 × 10$^6$ | 6.49 × 10$^6$ | 15.9% |
| Design 2 (bioinspired 3) | 86.6 | 7.64 × 10$^6$ | 6.65 × 10$^6$ | 14.9% |
| Design 2 (bioinspired 4) | 86.0 | 7.54 × 10$^6$ | 7.09 × 10$^6$ | 6.3% |
| Design 2 (bioinspired 5) | 88.1 | 7.89 × 10$^6$ | 7.15 × 10$^6$ | 10.3% |
| Features I, II, and III | | | | |
| Design 3 (T3 open surface) | 94.0 | 5.44 × 10$^6$ | 5.83 × 10$^6$ | 6.7% |
| Design 3 (B3 open surface) | 91 | 5.05 × 10$^6$ | 4.59 × 10$^6$ | 10.0% |
| Design 3 (T3 open surface without hole) | 62.3 | 5.98 × 10$^6$ | 5.82 × 10$^6$ | 2.7% |
| Design 3 (B3 open surface without hole) | 55.6 | 4.78 × 10$^6$ | 4.51 × 10$^6$ | 6.0% |
| Design 3 (T3 closed surface) | 96.0 | 11.04 × 10$^6$ | 11.51 × 10$^6$ | 4.1% |
| Design 3 (B3 closed surface) | 92.4 | 11.04 × 10$^6$ | 11.24 × 10$^6$ | 1.8% |
| Design 3 (T3 closed surface without hole) | 75.8 | 11.26 × 10$^6$ | 13.44 × 10$^6$ | 16.2% |
| Design 3 (B3 closed surface without hole) | 70.4 | 10.22 × 10$^6$ | 13.18 × 10$^6$ | 22.5% |

After design and printing according to the foregoing, the final part, Part (5)—cleaning and post-production processes, strictly followed the rules defined by FDA and ASTM standards.

Five parts or processes are thus involved in this methodology once Step 102 has been performed: Part (1) CAD design of the implant or plate using commercially available software, with reference to patient weight, fracture modelling, and Finite Element Analysis on the stress distribution of standard bone plate; Part (2) adjusting the location and number of screw holes, and contouring the standard bone plate to anatomy, to optimise the fitting and fixation of plate to fracture; Part (3) customizing the modulus of plate through optimizing the internal lattices and external shell structure with fully closed features or, alternatively, opened at the front comprising a solid edge and back; Part (4) using AM techniques to manufacture the plate; and Part (5) applying a suitable post-process (e.g. cleaning) for products from additive manufacturing.

Broadly speaking, therefore:

(1) The methodology for orthopaedic implants customization comprises using CAD customised shell design with optimized internal lattices and prototype manufacturing using selective laser melting method, wherein the stress-distribution on plate was illustrated using FEA. Thus, redundant screw holes can be removed while the functional screw holes can be placed patient specifically. Mathematical predictions on the modulus and bending stiffness then ensure the selection of solid shell and internal lattices match the condition of patient or the patient parameter(s) measured at Step 102 of FIG. 17.

(2) The methodology of (1), in an enhancement, can further include development of the three truss-based lattice structures designed to be produced by additive manufacturing methods. The first lattice unit for forming the first of the three lattice structures was modified from truncated lattices. The second lattice unit for forming the second of the three lattice structures was composed of a dodecahedral unit, and extra trusses were added to the surface of the lattice matrix to enhance bending stiffness. The third lattice unit for forming the third of the three lattice structures was modified from octahedral lattices, and additional supporting trusses were added to the surface layer of lattice matrix. Varies lattice designs, truss based or freeform structures, lightweight structures, as well as uniform or non-uniform porous structures, can be used as internal lattice matrix to tune the bending stiffness and modulus of plate.

(3) The methodology of (1) may further include the enhancement of predicting bending stiffness and modulus of plate, using correction factors defined based on testing the results from (2). The four-point bending tests strictly followed the ASTM F382 standard.

(4) The methodology of (1) may further include the enhancement of customizing an orthopaedic implant using internal lattices and a solid shell being either fully closed or opened, comprising edges and back, the location and number of screw holes being adjusted based on the fracture condition—i.e. the condition, shape and size of the fracture in the bone across which the implant is to be secured to arrange the bone to facilitate healing.

(5) The methodology of (3) may further include calculating the mechanical properties of parts containing anisotropic and isotropic lattices, non-uniform and uniform porous structures, freeform structures and lightweight structures.

Mismatches between the Young's modulus of bone and bone plate (i.e. orthopaedic implant—e.g. orthopaedic trauma plate) causes stress shielding, which can delay the healing process. Using the methods taught herein, orthopaedic implants can be developed that match the Young's modulus to that of the bone, while maintaining outer dimensions of the implant—e.g. to meet dimensions of current, standard solid implants. In this manner, the orthopaedic implants taught herein promote bone growth.

Due to the diverse nature of fractures, non-customized fitting in fracture fixation increases the risk of failure. For example, finite element analysis was conducted using commercially available bone plates, while the 3D tibia model was obtained from a computer tomography (CT) scan of human cadaveric tibia (FIG. 1). Results suggested that stress concentration regions are located nearby redundant screw holes. By removing unnecessary screw holes, by positioning the screw holes in locations optimised for the particular fracture experienced by the subject, and in customising the trajectories of the screw holes to facilitate optimal anchoring without creating stress raisers, such stress concentrations can largely be avoided.

The methods taught herein have successfully demonstrated the methodology for altering the Young's modulus (i.e. mechanical elastic property) of orthopaedic implants using additive manufacturing technology, while maintaining adequate strength of the device. This can be used in a mass produced or customised process.

This methods taught herein also demonstrate implant modulation through optimizing the internal structure of an orthopaedic plate. The bending structural stiffness of the plate design can be accurately predicted and is close to the prototype tested according to ASTM F382.

The new plate or implant design taught herein can potentially lead to greater union rates (healing) and fewer delayed and non-unions. In addition, customization enables better fitting both biomechanically (Young's modulus) and anatomically to the fracture and bone contour to achieve better healing experience. This has been demonstrated herein for customizing bone plates for tibial fractures. This present methods can further be used for more complex anatomically shaped fixation plates such as pelvic plates, proximal and distal femoral plates, forearm and humeral plates, and in place of other fixation devices e.g. intra-medullary nails and even replacement implants (e.g. hip and knee replacements).

Further embodiments of the present teachings provide Orthopaedic implants in which the implant itself is one or both of osteoinductive (induce osteocyte to form bone) and osteoconductive (provide a structure for osteocytes to grow along). This may be achieved using surface topography modifications such by providing nanostructured, nanotopographically altered or nanotextured surfaces—particularly the surface that will face the bone, in use. This may also be achieved by selecting the internal lattice structure to promote formation and oriented growth of osteoctyes. Using AM processes described above, structures can be designed that incorporate the texturing—e.g. osteoinductive or osteoconductive texturing—into the implant at the of manufacture, such that the resulting implant is one or both of osteoinductive and osteoconductive. Moreover, such texturing may only be applied to the surface facing the bone and, even then, may only be selectively applied to facilitate localised bone growth. Hence, implants taught herein may not only be used as a form of stabilization but also as a tool to initiate and guide bone growth across the fracture site.

Other implementations of the present teachings will be apparent to those skilled in the art from consideration of the specification and practice of the teachings of the present application. Various aspects and/or components of the described example implementations may be used singly or in any combination. It is intended that the specification and example implementations be considered as examples only, with the true scope and spirit of the present application being indicated by the following claims.

Throughout this specification and the statements which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. An orthopaedic implant formed for a specific subject, the orthopaedic implant being formed in accordance with specifications, the specifications comprising an elasticity, a length, and positions of two or more fixation locations by which to fix the orthopaedic implant to a bone of the specific subject, the specifications being determined from a weight of the subject and the bone of the specific subject, wherein each fixation location comprises a longitudinal axis through the orthopaedic_implant along a trajectory of the longitudinal axis calculated to optimise an anchoring direction of an anchor used with the orthopaedic implant, and the fixation locations are located relative to one another to reduce creation of localised stresses in the bone after fixation of the orthopaedic implant thereto, the implant further comprising a solid shell with an internal lattice structure in the solid shell, wherein the solid shell fully encloses the internal lattice structure.

2. The orthopaedic implant of claim 1, wherein the elasticity is calculated based on an expected natural flexibility of the bone.

3. The orthopaedic implant of claim 2, wherein the elasticity is calculated based on a weight of the specific subject.

4. The orthopaedic implant of claim 1, wherein each fixation location is arranged to cooperate with a respective screw.

5. The orthopaedic implant of claim 1, comprising an internal lattice structure to maintain outer dimensions of the orthopaedic implant while reducing resistance to bending.

6. The orthopaedic implant of claim 1, wherein the solid shell is open and is formed as a solid edge and back of the orthopaedic implant, and a front of the orthopaedic implant is at least partially omitted so the internal lattice structure is at least partially exposed to the bone.

7. The orthopaedic implant of claim 6, wherein a type of the internal lattice structure is selected to promote one or both of osteoinduction and osteoconduction.

8. The orthopaedic implant of claim 1, wherein a surface topography of the orthopaedic implant is modified to promote one or both of osteoinduction and osteoconduction.

9. The orthopaedic implant of claim 1, wherein the orthopaedic implant is an orthopaedic trauma plate.

* * * * *